United States Patent [19]

Miller et al.

[11] 4,085,209

[45] Apr. 18, 1978

[54] PREPARATION AND SAFENING EFFECT OF 1-SUBSTITUTED IMIDAZOLE METAL SALT COMPLEXES

[75] Inventors: George Allen Miller, Glenside; Harold Edwin Carley, Chalfont, both of Pa.

[73] Assignee: Rohm and Haas Company, Philadelphia, Pa.

[21] Appl. No.: 547,290

[22] Filed: Feb. 5, 1975

[51] Int. Cl.² .......................... C07F 3/06; C07F 3/00; C07F 1/00; A01N 9/22
[52] U.S. Cl. .................... 424/245; 260/299; 424/273 R; 548/335; 548/337; 548/341
[58] Field of Search ............... 260/299, 309; 424/245, 424/273

[56] References Cited

U.S. PATENT DOCUMENTS

| | | | |
|---|---|---|---|
| 3,285,921 | 11/1966 | Ortner et al. | 260/270 |
| 3,575,999 | 4/1971 | Godefroi et al. | 260/309 |
| 3,647,810 | 3/1972 | Bayer et al. | 260/299 |
| 3,658,813 | 4/1972 | Godefroi et al. | 260/240 K |
| 3,796,704 | 3/1974 | Metzger et al. | 260/240 K |
| 3,821,394 | 6/1974 | Timmler et al. | 424/273 |
| 3,843,667 | 10/1974 | Cupery | 260/299 |

OTHER PUBLICATIONS

Garnovskii et al., Chemical Abstracts, vol. 65, 11742(f), 1966.
Draber et al., Chemical Abstracts, vol. 74, 125697s, (1971).
Buechel et al., Chemical Abstracts, vol. 74, 125698t, (1971).

*Primary Examiner*—Donald G. Daus
*Assistant Examiner*—Diana G. Rivers
*Attorney, Agent, or Firm*—Bernard J. Burns; George W. F. Simmons; William E. Lambert

[57] ABSTRACT

This invention concerns the preparation of 1-substituted imidazole metal salt complexes and their use particularly as systemic fungicides. The preparation of the metal salt complexes of these imidazoles produces a safening effect, i.e., the ability to reduce undesirable plant growth regulatory activity and phytotoxicity while retaining the efficacy of the compounds against phytopathogenic fungi.

10 Claims, No Drawings

PREPARATION AND SAFENING EFFECT OF 1-SUBSTITUTED IMIDAZOLE METAL SALT COMPLEXES

SUMMARY OF THE INVENTION

It has recently been shown that certain substituted imidazoles possess fungicidal activity but are of limited utility since they are phytotoxic to many agronomic plant species. The limited utility of these substituted imidazoles is due to their inherent phytotoxicity and undesirable growth regulatory response. Thus, there is a need for an imidazole fungicide that would be effective on both monocotyledons and dicotyledons but which does not have the undesirable phytotoxicity which present imidazole fungicides possess. The metal salt complexes of the substituted imidazoles of this invention do fulfill this need and are excellent systemic fungicidal agents against phytopathogenic fungi. They also have the advantage that they are safened for both monocotyledons and dicotyledons.

This safening effect is an ability to reduce the phytotoxicity of the free imidazole base while maintaining its systemic fungicidal activity. As the free base, these 1-substituted imidazoles can cause severe injury to the foliage and flowers of certain plants, in particular to dicotyledonous plants. At the prescribed use rates, these free bases can be used only on certain monocotyledonous plants since as noted above they produce phytotoxic and undesirable growth regulatory responses in dicotyledonous plants. Even though these compounds as the free base exhibit fungicidal activity on monocotyledonous plants their detrimental effects make them an undesirable choice for the control of phytopathogenic fungi on dicotyledonous plants. The metal salt complexes of this invention are safened and effective systemic fungicides for both monocotyledonous and dicotyledonous plants.

This invention is concerned with imidazole metal salt complexes of the formula

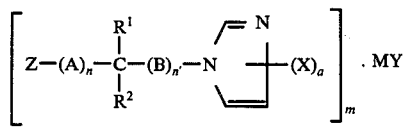
(I)

wherein Z is a phenyl group or a substituted phenyl group of from 6 to 10 carbon atoms, a naphthyl group or a substituted naphthyl group from 10 to 14 carbon atoms, a furanyl group, a benzofuranyl group, a thienyl group, an alkyl group of from 1 to 8 carbon atoms which may be branched or straight chained or a cycloalkyl group of from 6 to 8 carbon atoms. $R^1$ is a hydrogen atom and $R^2$ is independently a hydrogen atom, an alkoxy group of from 1 to 8 carbon atoms, an alkenoxy group of from 2 to 8 carbon atoms, an alkynoxy group of from 2 to 8 carbon atoms, an alkylthio group, a halogen atom, a hydroxy group, an acetoxy group, a benzoyloxy group, an alkylamino group of from 1 to 4 carbon atoms, a phenylhydrazino group of from 6 to 10 carbon atoms; or $R^1$ and $R^2$ can be taken together with attached carbon atom to form a ketone group, a ketal group, a thioketal group, a hydroxyimino group, an alkylimino group of from 1 to 4 carbon atoms or a phenylhydrazone group of from 6 to 10 carbon atoms. A and B are divalent alkylene groups of from 1 to 4 carbon atoms which can be branched or straight chain. X is a methyl group or a halogen atom replacing a hydrogen atom on the ring; $a$ is an integer from 0 to 3; and $n$ and $n'$ are integers from 0 to 2. M is a metal cation which can be selected from Groups IIA, IVA, IB, IIB, VIB, VIIB and VIII of the Periodic Table. Y is an anion counterion and $m$ is an integer from 1 to 4.

The preferred metal salt complexes of this invention are those in which Z is phenyl or substituted phenyl of from 6 to 10 carbon atoms, most preferably phenyl substituted with up to 2 substituents such as fluoro, chloro, bromo, iodo, nitro, trihalomethyl, methyl, ethyl, methoxy, ethoxy and the like.

The more preferred metal salt complexes of this invention are those in which Z is defined as above and $R^1$ and $R^2$ when taken together form a ketone or a ketal or when $R^1$ is a hydrogen atom and $R^2$ is independently a hydrogen atom, an alkoxy group, an alkenoxy group or an alkynoxy group.

The metal salt complexes of these 1-substituted imidazoles can be prepared by adding a stoichiometric amount of a metal salt dissolved in an appropriate solvent to the 1-substituted imidazole dissolved in a similarly appropriate solvent. The reaction mixture is briefly stirred and the solvent is removed under reduced pressure to give a solid metal salt complex of the respective 1-substituted imidazole.

The metal salt complex can also be prepared by mixing in a spray tank stoichiometric or excess amounts of the metal salt and 1-substituted imidazole in an agronomically acceptable carrier containing the appropriate adjuvants just prior to spraying the plants. Adjuvants that may be included in this "in-situ" preparation may be detergents, emulsifiers, wetting agents, spreading agents, dispersing agents, stickers, adhesives, and the like which are used in agricultural applications.

Solvents that can be utilized in these procedures include polar solvents e.g., water, methanol, ethanol, isopropanol or ethylene glycol and aprotic dipolar solvents, e.g., dimethylsulfoxide, acetonitrile, dimethylformamide, nitromethane or acetone.

The metal salt cations that may be used in making these complexes include calcium, magnesium, manganese, copper, nickel, zinc, iron, cobalt, tin, cadmium, mercury, chromium, lead, barium, and the like.

Any appropriate anion e.g., chloride, bromide, iodide, sulfate, bisulfate, phosphate, nitrate, perchlorate, carbonate, bicarbonate, hydrosulfide, hydroxide, acetate, oxalate, malate, citrate, ethylene-bis-dithiocarbamate and the like may be utilized as the counterion in the metal salt.

It has been found that metal containing fungicides can act as safening agents when used in place of metal salts. Typical metal containing fungicides that can be utilized in these procedures are:

a. dithiocarbamates and derivatives such as:
   ferric dimethyldithiocarbamate (ferbam),
   zinc dimethyldithiocarbamate (ziram),
   manganese ethylenebisdithiocarbamate (maneb) and its coordination product with zinc ion (mancozeb),
   zinc ethylenebisdithiocarbamate (zineb);

b. copper-based fungicides such as:
   cuprous oxide,
   copper naphthenate, and
   Bordeaux mixture; and c. miscellaneous fungicides such as:
   phenylmercuric acetate N-ethylmercuri-1,2,3,6-tetrahydro-3,6-endomethano-3,4,5,6,7,7'-hexachlorophthalimide, phenylmercuri monoethanolammonium lactate nickel-containing compounds and calcium cyanamide.

The following examples are provided to illustrate the method of preparation of the metal complex salts of this invention and are not to be considered as limitations of the scope thereof.

EXAMPLE I

Preparation of bis 1-(β-allyloxy-2,'4'-dichlorophenethyl) Imidazole Zinc Chloride To a solution of 1 g. (0.0036 mole) of 1-(β-allyloxy-2',4'-dichlorophenethyl) imidazole in 10 ml. of anhydrous methanol was added dropwise a solution of 0.23 g. (0.00168 mole) of $ZnCl_2$ dissolved in 20 ml. of methanol. The clear solution was concentrated under reduced pressure to give a yellowish hygroscopic solid mp. 49°–54°.

Anal. Calc'd for $C_{28}H_{28}Cl_6N_4O_2Zn$: Found: C, 46.03; H, 3.86; Cl, 29.11; N, 7.67; O, 4.38; Zn, 8.95; theory C, 45.90; H, 3.88; Cl, 28.59; N, 8.02; O, 5.48; Zn, 7.57.

EXAMPLE II 1-(β-allyloxy-2',4'-dichlorophenethyl)-imidazole zinc chloride 1-(β-allyloxy-2',4'-dichlorophenethyl)-imidazole 2.4 g. (0.008 mole) and $ZnCl_2$ 1.1 g. (0.008 mole) are mixed in an acetone: methanol: water (1:1:2) solvent (40 ml.). This preparation is immediately applied to plant foliage.

The zinc chloride complex of the following examples are prepared by the procedure of Example I or Example II when the free base of the appropriate imidazole and zinc chloride are utilized.

EXAMPLES III TO XXXVIII $$Z-(A)_n-\underset{R^2}{\overset{R^1}{\underset{|}{\overset{|}{C}}}}-(B)_{n'}-N\underbrace{\phantom{xxx}}_{}\overset{\displaystyle\diagup=N}{\phantom{x}}-(X)_a \cdot HA$$

| Example No. | Z | $(A)_n$ | $(B)_{n'}$ | $R^1$ | $R^2$ | $(X)_a$ | HA |
|---|---|---|---|---|---|---|---|
| III | 2-chlorophenyl | — | $CH_2$ | H | $-OC_2H_5$ | — | $HNO_3$ |
| IV | 2,5-dichlorophenyl | " | " | " | $-OC_4H_9$ | " | " |
| V | 2,4-dichlorophenyl | " | " | " | $-OC_8H_{17}$ | " | " |
| VI | " | $CH_2$ | " | " | $-OCH_2CH=CH_2$ | " | HCL |
| VII | " | $CH_2CH_2$ | " | " | " | " | $HNO_3$ |
| VIII | " | — | $CHCH_3$ | " | " | " | " |
| IX | " | " | $CH_2$ | " | " | " | — |
| X | " | " | " | \multicolumn{2}{c|}{=O} | " | " |
| XI | " | " | " | " | " | " | $HNO_3$ |
| XII | " | " | " | " | " | 4-$NO_2$ | — |
| XIII | " | " | " | " | " | 4,5 di-Cl | " |
| XIV | phenyl | " | " | \multicolumn{2}{c|}{$-OCH_2CH_2O-$} | — | $HNO_3$ |
| XV | 4-chlorophenyl | — | " | " | " | — | — |
| XVI | 4,5-dichlorophenyl | " | " | " | " | " | $HNO_3$ |
| XVII | 4-nitrophenyl | " | " | " | " | " | " |
| XVIII | 2-furanyl | " | " | " | " | " | " |
| XIX | 2-thienyl | " | " | " | " | " | " |
| XX | 3-(2,5-dichlorothienyl) | " | " | " | " | — | $HNO_3$ |
| XXI | cyclohexyl | " | " | " | " | " | " |
| XXII | hexyl | " | " | " | " | " | " |
| XXIII | 2,4-dichlorophenyl | " | " | " | " | 2-$CH_3$ | — |
| XXIV | " | " | " | H | OH | — | $HNO_3$ |
| XXV | " | " | " | " | Cl | " | HCL |
| XXVI | " | " | " | " | $OCOCH_3$ | " | $HNO_3$ |
| XXVII | " | " | " | " | $OCOC_6H_5$ | " | HCL |
| XXVIII | " | " | " | \multicolumn{2}{c|}{$=NC_4H_9$} | " | " |
| XXIX | " | " | " | H | $NHC_4H_9$ | " | HCL |
| XXX | " | " | " | \multicolumn{2}{c|}{$=NNC_6H_5$} | " | — |
| XXXI | " | " | " | H | $NHNHC_6H_5$ | " | " |
| XXXII | " | — | " | H | CHN (ring) | — | — |
| XXXIII | " | " | " | \multicolumn{2}{c|}{=NOH} | " | " |
| XXXIV | " | " | " | H | $SC_4H_9$ | " | " |
| XXXV | " | " | " | " | H | " | " |
| XXXVI | Cl—⟨phenyl⟩—CH=CH—N⟨imidazole⟩ | | | | | | |
| XXXVII | benzofuran-C(OCH₂O)-CH₂-N⟨imidazole⟩ | | | | | | |

In the above examples I to XXXVII any appropriate metal salt or metal containing fungicide such as zinc chloride, manganese sulfate, cupric bromide, cobaltous nitrate, chromic chloride, ferric sulfate, cadmium nitrate, mercuric chloride, calcium oxalate, calcium carbonate, nickel acetate, stannous iodide, barium hydroxide, magnesium citrate, magnesium perchlorate lead nitrate, mancozeb, Bordeaux mixture, phenylmercuric acetate and the like can be utilized.

The metal salt complexes of these imidazole derivatives are excellent safened systemic eradicant fungicides and possess a high degree of activity against a wide variety of phytopathogenic fungi. The compounds are particularly effective for the control of broad bean grey mold (*Botrytis cinerea*) on faba bean, rice rice blast (*Piricularia oryzae*) on rice plants, tomato late blight (*Phytophthora infestans*) on tomato seedlings, bean powdery mildew, (*Erysiphe polygoni*) on bean plants, barley net blotch (*Helminthosporium teres*) on barley plants, grape downy mildew (*Plasmopora viticola*) on grape seedlings, citrus decay (*Penicillium digitatum*) on citrus fruit, apple scab (*Venturia inequalis*) on apple seedlings, powdery mildew (*Erysiphe graminis*) on wheat plants and powdery mildew (*Sphaerothecia fulgininea*) on cucumber plants.

In evaluating these compounds a preliminary fungicidal evaluation is carried out using the compounds at an application rate of 2400 ppm based on the free base in a suitable carrier, and spraying the plants to run off. The ability of these metal salt complexes to safen the imidazoles against injury to the plant foliage and flowers while maintaining their systemic fungicidal efficacy is demonstrated in the following series of Tables I through VII.

Table I shows the safening effect of the metal salt complexes of 1-($\beta$-allyloxy-2',4'-dichlorophenethyl-)imidazole as prepared via Example II using zinc chloride, manganese sulfate and cupric sulfate as the metal salts. Various concentrations of the metal salt complexes given are based on the free base. An equivalent mole to mole ratio of metal salt is utilized in the procedure for their preparation. A comparision of the effects of the metal salts themselves is given in the table along with the effect of the free base of the imidazole at the various concentrations utilized in the metal salt complexes. Tomato seedlings in the 3–4 leaf stage of development are used in this test.

Table I

| Treatment | Concentration in ppm based on free base | Phytotoxicity Index[a] (× 2 replicates) |
|---|---|---|
| Imidazole (90% EC[b]) free base | 600 | 2.0 |
| Imidazole (90% EC[b]) free base | 1200 | 3.0 |
| Imidazole (90% EC[b]) free base | 2400 | 4.5 |
| ZnCl₂ | 280 | 0 |
| ZnCl₂ | 560 | 0 |
| ZnCl₂ | 1120 | 1.0 |
| MnSO₄ | 340 | 0 |
| MnSO₄ | 680 | 0 |
| MnSO₄ | 1360 | 0 |
| CuSO₄ | 320 | 0 |
| CuSO₄ | 640 | 0 |
| CuSO₄ | 1280 | 0 |
| Example II (ZnCl₂) | 600 | 0 |
| Example II (ZnCl₂) | 1200 | 0 |
| Example II (ZnCl₂) | 2400 | 0.3 |
| Example II (MnSO₄) | 600 | 2.0 |
| Example II (MnSO₄) | 1200 | 3.0 |
| Example II (MnSO₄) | 2400 | 4.5 |
| Example II (CuSO₄) | 600 | 0 |
| Example II (CuSO₄) | 1200 | 1.0 |
| Example II (CuSO₄) | 2400 | 2.0 |

[a] 0 = No observable injury; 5 = death of tomato seedlings
[b] EC = emulsifiable concentrate Test data which demonstrates that the efficacy of the 1-($\beta$-allyloxy-2',4'-dichlorophenethyl) imidazole, prepared via Example II, against apple scab (*Venturia inaequalis*) is not diminished by safening it via the metal salt complex formation, is given in Table II. The concentration given is based on the free base of the imidazole.

Table II

| Treatment | Concentration ppm | Phytotoxicity Index Apple Seedlings[a] (× 3 Replicates) | % Apple Scab Control (× 3 Replicates) |
|---|---|---|---|
| Imidazole free base | 2400 | 5.0 | — |
| | 1200 | 3.0 | — |
| | 600 | 2.2 | 100 |
| | 300 | 0.8 | 100 |
| Example II | 2400 | 0 | 100 |
| | 1200 | 0 | 100 |
| | 600 | 0 | 100 |
| | 300 | 0 | 100 |

[a] 0 = No observable injury; 5 = death of apple seedlings

The phytotoxicity of 1-($\beta$-allyloxy-2',4'-dichlorophenethyl) imidazole and the safening effect of the zinc chloride complex prepared via Example II on cucumber is given in Table III below. The concentrations are based on the free base of the imidazoles.

Table III

| Treatment | ppm | Phytotoxicity Index[a] (× 3 Replicates) |
|---|---|---|
| Imidazole free base (90% EC) | 600 | 2.0 |
| Imidazole free base (90% EC) | 1200 | 3.3 |
| Imidazole free base (90% EC) | 2400 | 5.0 |
| Example II | 600 | 0 |
| Example II | 1200 | 0.13 |
| Example II | 2400 | 0.2 |
| Untreated control | | 0 |

[a] 0 = No observable injury; 5 = Death of assay plants

The duration and fungicidal efficacy of 1-($\beta$-allyloxy-2',4'-dichlorophenethyl) imidazole and its metal salt complex as prepared via Example II are given in Table IV. This data was obtained against barley net blotch (*Helminthosporum teres*) and the concentration given is based on the free base of the imidazole.

Table IV

| Treatment | Concentration ppm | Inoculation-Days after Chemical application | Disease Control Level[a] |
|---|---|---|---|
| Imidazole free base (90% EC) | 150 | 3 | A |
| | | 6 | B |
| Imidazole free base (90% EC) | 75 | 3 | A |
| Imidazole free base (90% EC) | 37.5 | 3 | A |
| | | 6 | D |
| Example II | 150 | 3 | A |
| | | 6 | B |
| Example II | 75 | 3 | A |
| | | 6 | B |
| Example II | 37.5 | 3 | A |
| | | 6 | D |
| ZnCl₂ | 80 | 3 | E |
| | | 6 | E |
| Example II | 40 | 3 | E |
| | | 6 | E |
| Example II | 20 | 3 | E |
| | | 6 | E |

[a] A = 97–100%; B = 90–96%; C = 70–89%; D = 50–69%; E = <50% Disease Control.

In Tables V and VI the safening effect of mancozeb (a zinc complex of manganese ethylene bisdithiocarbamate) on 1-($\beta$-allyloxy-2',4'-dichlorophenethyl) imidazole is demonstrated. These complexes were prepared via the procedure of Example II utilizing a weight per weight ratio instead of a molar ratio.

Table V

| Treatment | Ratio Mancozeb:Imidazole (lb./100 Gal.) | Phytotoxicity Index[a] (× 3 replicates) |
|---|---|---|
| Mancozeb | 1:0 | 0 |
| Mancozeb | 2:0 | 0 |
| Imidazole (90% EC) | 0:½ | 4.0 |
| Imidazole (90% EC) | 0:1 | 4.7 |
| Imidazole (90% EC) | 0:2 | 5.0 |
| Example II (mancozeb) | 1:½ | 0.2 |
| Example II (maneozeb) | 1:1 | 3.0 |
| Example II (mancozeb) | 1:2 | 4.3 |
| Example II (mancozeb) | 2:½ | 0.5 |
| Example II (mancozeb) | 2:1 | 2.7 |
| Example II (mancozeb) | 2:2 | 3.0 |

[a] 0 = No observable injury; 5 = tomato seedlings dead

The data in Table VI gives the fungicidal efficacy of the mancozeb complex of 1-(β-allyloxy-2',4'-dichlorophenyl) imidazole versus bean powdery mildew (*Erysiphe polygoni*). Concentrations are based on the free base and the complex is prepared via Example II using a 1:1 wt/wt. ratio of mancozeb to imidazole.

Table VI

| Treatment | Concentration in ppm. | % Control of Bean Powdery Mildew[a] |
|---|---|---|
| Imidazole (90% EC) | 50 | 100 |
| Imidazole (90% EC) | 25 | 100 |
| Imidazole (90% EC) | 12.5 | 100 |
| Imidazole (90% EC) | 6.3 | 100 |
| Mancozeb | 50 | 83 |
| Mancozeb | 25 | 82 |
| Mancozeb | 12.5 | 73 |
| Example II (mancozeb) | 6.3 | 70 |
| Example II (mancozeb) | 50 | 100 |
| Example II (mancozeb) | 25 | 100 |
| Example II (mancozeb) | 12.5 | 100 |
| Example II (mancozeb) | 6.3 | 100 |

[a] % Control = $\frac{\bar{x}\ \text{Control lesions} - \bar{x}\ \text{treatment lesions}}{\bar{x}\ \text{Control Lesions}} \times 100$ A comparison of the safening effects of ZnCl₂ complexes of various analogs of 1-(β-allyloxy 2',4'-dichlorophenethyl) imidazole versus their free based are given in Table VII. The compounds were applied to the plant foliage at the rate of 2400 ppm based on the free base of the imidazole. The complexes were prepared according to Example II wherein a 1:1 ratio of metal salt to imidazole was utilized.

Table VII

| Example No. | Phytotoxicity Index[a] (x̄ 3 Replicates) | |
|---|---|---|
| | Tomato | Cucumber |
| III | 5.0 | 4.0 |
| III Complex | 2.3 | 2.3 |
| IV | 5.0 | 5.0 |
| IV Complex | 4.7 | 4.7 |
| V | 5.0 | 4.3 |
| V Complex | 2.6 | 1.0 |
| VI | 5.0 | 5.0 |
| VI Complex | 2.3 | 2.6 |
| VII | 5.0 | 5.0 |
| VII Complex | 3.6 | 2.0 |
| VIII | 5.0 | 5.0 |
| VIII Complex | 0 | 2.0 |
| IX | 5.0 | 5.0 |
| IX Complex | 2.6 | 0.3 |
| X | 0 | 3.3 |
| X Complex | 1.0 | 1.0 |
| XI | 0 | 1.3 |
| XI Complex | 0 | 1.0 |
| XII | 0 | 3.0 |
| XII Complex | 0 | 0.3 |
| XIII | 0 | 1.3 |
| XIII Complex | 0 | 1.0 |
| XIV | 1.0 | 3.0 |
| XIV Complex | 0 | 1.6 |
| XV | 2.6 | 3.3 |
| XV Complex | 1.0 | 1.6 |
| XVI | 4.0 | 4.0 |
| XVI Complex | 0 | 1.0 |
| XVII | 0 | 1.0 |
| XVII Complex | 0 | 1.0 |
| XVIII | 0 | 1.6 |
| XVIII Complex | 0 | 1.0 |
| XIX | 2.0 | 3.0 |
| XIX Complex | 1.0 | 2.0 |
| XX | 4.6 | 4.3 |
| XX Complex | 1.3 | 3.0 |
| XXI | 3.6 | 4.0 |
| XXI Complex | 1.0 | 3.3 |
| XXII | 4.6 | 4.0 |
| XXII Complex | 0.3 | 2.0 |
| XXIII | 3.0 | 4.0 |
| XXIII Complex | 2.0 | 2.0 |
| XXIV | 0 | 1.3 |
| XXIV Complex | 0 | 1.0 |
| XXV | 5.0 | 5.0 |
| XXV Complex | 3.6 | 3.3 |
| XXVI | 3.0 | 3.6 |
| XXVI Complex | 0 | 1.0 |
| XXVII | 1.0 | 1.0 |
| XXVII Complex | 0 | 0 |
| XXVIII | 0 | 1.0 |
| XXVIII Complex | 0 | 0 |
| XXIX | 5.0 | 5.0 |
| XXIX Complex | 0 | 1.0 |
| XXX | 0 | 1.0 |
| XXX Complex | 0 | 0 |
| XXXI | 0 | 2.0 |
| XXXI Complex | 0 | 0.3 |
| XXXII | 0 | 2.0 |
| XXXII Complex | 0 | 2.0 |
| XXXIII | 0 | 0 |
| XXXIII Complex | 0 | 0 |
| XXXIV | 5.0 | 5.0 |
| XXXIV Complex | 5.0 | 5.0 |
| XXXV | 4.0 | 4.0 |
| XXXV Complex | 3.6 | 3.0 |
| XXXVI | 3.3 | 4.0 |
| XXXVI Complex | 0 | 3.0 |
| XXXVII | 2.6 | 3.0 |
| XXXVII Complex | 2.0 | 2.0 |

[a] 0 = No observable injury to bioassay plant: 5 = Death of Bioassay plant

The metal salt complexes of this invention are useful as safened agricultural systemic fungicides and as such may be applied to various loci such as the seed, the soil or the foliage. For such purposes these compounds may be used in the technical or pure form as prepared, as solutions or as formulations. The compounds are usually taken up in a carrier or are formulated so as to render them suitable for subsequent dissemination as fungicides. For example, these imidazole metal salt complexes may be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art may be found in the John W. McCutcheon, Inc. publication "Detergents and Emulsifiers Annual."

In general, the complexes of this invention are somewhat limited in solubility but they may be dissolved in certain solvents such as acetone, methanol, ethanol, dimethylformamide, pyridine or dimethyl sulfoxide and such solutions extended with water. The concentration of the solution may vary from 2% to 50% with a preferred range being 5% to 25%.

For the preparation of emulsifiable concentrates, the complexes may be dissolved in suitable organic solvents, or a mixture of solvents, together with a emulsifying agent which permits dispersion of the fungicide in water. The concentration of the active ingredient in emulsifiable concentrates is usually 10% to 25% and in flowable emulsion concentrates, this may be as high as 75%.

Wettable powders suitable for spraying, may be prepared by admixing the compounds with a finely divided solid, such as clays, inorganic silicates and carbonates, and silicas and incorporating wetting agents, and/or dispersing agents in such mixtures. The concentration of active ingredients in such formulations is usually in the range of 20% to 98%, preferably 40% to 75%. A typical wettable powder is made by blending 50 parts of 1-($\beta$-allyloxy-2',4'-dichlorophenethyl) imidazole zinc chloride, 45 parts of a synthetic precipitated hydrated silicon dioxide sold under the trademark Hi-Sil ®, and 5 parts of sodium lignosulfonate (Marasperse ® N-22). In another preparation a kaolin type (Barden) clay is used in place of the Hi-Sil in the above wettable powder, and in another such preparation 25% of the Hi-Sil is replaced with a synthetic sodium silico aluminate sold under the trademark Zeolex ® 7.

Dusts are prepared by mixing the imidazole metal salt complex with finely divided inert solids which may be organic in nature. Materials useful for this purpose include botanical flours, silicas, silicates, carbonates and clays. One convenient method of preparing a dust is to dilute a wettable powder with a finely divided carrier. Dust concentrates containing 20% to 80% of the active ingredient are commonly made and are subsequently diluted to 1% to 10% use concentration.

The imidazole metal salt complexes can be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application and diseases to be controlled, but the preferred effective amount is usually about 0.1 lb. to 25 lbs. per acre of the active ingredient.

As a seed protectant, the amount of toxicant coated on the seed is usually at a dosage rate of about 0.1 to 20 ounces per hundred pounds of seed. As a soil fungicide the chemical may be incorporated in the soil or applied to the surface usually at a rate of 0.1 to 50 lbs. per acre, preferably at a rate of 50 lbs. per acre for soil application. As a foliar fungicide, the toxicant is usually applied to growing plants at a rate of 0.1 to 10 pounds per acre.

Fungicides which may be combined with the fungicides of this invention include:

(a) Dithiocarbamates and derivatives such as: Ferric dimethyldithiocarbamate (ferbam), zinc dimethyldithiocarbamate (ziram), manganese ethylenebisdithiocarbamate (maneb) and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), and 3,5-dimethyl-1,3,5,2H-tetrahydrothiadiazine-2-thione (dazomet);

(b) Nitrophenol derivatives such as: Dinitro-(1-methylheptyl) phenyl crotonate (dinocap), 2-sec-butyl-4,6-dinitrophenyl-3,3-dimethyl acrylate (binapacryl), and 2-sec-butyl-4,6-dinitrophenyl isopropyl carbonate;

(c) Heterocyclic structures such as: N-trichloromethylthiotetrahydro-phthalimide (captan), N-trichloromethylthiophthalimide (folpet), 2-heptadecyl-2-imidazoline acetate (glyodine), 2-octylisothiazolone-3,2,4-dichloro-6-(o-chloroanilino)-s-triazine, diethyl phthalimidophosphorothioate, 4-butyl-1,3,4,-triazole, 5-amino-1-[bis(dimethylamino) phosphinyl]-3-phenyl-1,2,4-triazole, 5-ethoxy-3-trichloromethyl-1,2,4-thiadizole, 2,3-dicyano-1,4-dithiaanthraquinone (dithianon), 2-thio-1,3-dithio-(4,5-b) quinoxaline (thioquinox), methyl 1-(butylcarbamoyl)-2-benzimidazole carbamate (benomyl), 2-(4-thiazolyl) benzimidazole (thiabendazole), 4-(2-chlorophenylhydrazono)-3-methyl-5-isoxazolone, pyridine-2-thiol-1-oxide, 8-hydrozyquinoline sulfate, 2,3-dihydro-5-carboxanilido-6-methyl-1,4-oxathiin-4,4-dioxide, 2,3-dihydro-5-carboxanilido-6-methyl-1,4-oxathiin,$\alpha$-(phenyl)-$\alpha$-(2,4-dichlorophenyl)-5-pyrimidinyl-methanol (triarimol), cis-N-[1,1,2,2-tetrachloroethyl)thio]-4-cyclohexene-1,2-dicarboximide, 3-[2-(3,5-dimethyl-2-oxycyclohexyl-2-hydroxy] glutarimide (cycloheximide), dehydroacetatic acid, N-(1,1,2,2-tetrachloroethylthio)-3a,4,7,7a-tetrahydrophthalimide (captafol), 5-butyl-2-ethylamino-4-hydroxy-6-methyl-pyrimidine (ethirimol), acetate of 4-cyclododecyl-2,6-dimethylmorpholine (dodemorph), and 6-methyl-2-oxo-1,3-dithiolo(4,5-b) quinoxaline (quinomethionate);

(d) Miscellaneous halogenated fungicides such as: Tetrachloro-p-benzoquinone (chloranil), 2,3-dichloro-1,4-naphthoquinone(dichlone), 1,4-dichloro-2,5-dimethoxybenzene (chloroneb), 3,5,6-trichloro-o-anisic acid (tricamba), 2,4,5,6-tetrachloroisophthalonitrile (TCPN), 2,6-dichloro-4-nitroaniline (dicloran), 2-chloro-1-nitropropane, polychloronitrobenzenes such as: penthachloronitrobenzene (PCNB) and tetrafluorodichloroacetone;

(e) Fungicidal antibiotics such as: Griseofulvin, kasugamycin and streptomycin;

(f) Copper-based fungicides such as: Cuprous oxide, basic cupric chloride, basic copper carbonate, copper naphthenate, and Bordeaux mixture; and (g) Miscellaneous fungicides such as: Diphenyl, dodecylguanidine acetate (dodine), phenylmercuric acetate, N-ethylmercuri-1,2,3,6-tetrahydro-3,6-endomethano-3,4,5,6,7,7-hexachlorophthalimide, phenylmercuric monoethanolammonium lactate, p-dimethylaminobenzenediazo sodium sulfonate, methylisothiocyanate, 1-thiocyano-2,4-dinitrobenzene, 1-phenythiosemicarbazide, nickel-containing compounds, calcium cyanamide, lime sulfur, sulfur, and 1,2-bis(3-methoxycarbonyl-2-thioureido)benzene (thiophanate-methyl).

The metal salt complexes of this invention can be advantageously employed in various ways. Since these metal salt complexes possess inherent systemicity and broad spectrum fungicidal activity they can be employed in the storage of cereal grain. These complexes can also be employed as fungicides in turf and fruit orchard applications. Other applications of the metal salt complexes of this invention will suggest themselves to those skilled in the art of agriculture and horticulture.

We claim:

1. A metal salt complex of the formula

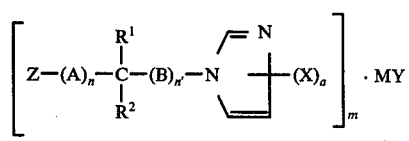

wherein Z is phenyl substituted with up to two substituents selected from the group consisting of fluoro, chloro, bromo, iodo, nitro, trihalomethyl, methyl, ethyl, methoxy and ethoxy; naphthyl furanyl; benzofuranyl; thienyl or halothienyl;

$R^1$ is hydrogen;

$R^2$ is independently selected from the group consisting of hydrogen, $(C_1-C_8)$ alkoxy, $(C_2-C_8)$ alkenoxy, $(C_2-C_8)$ alkynoxy $(C_1-C_8)$ alkylthio, halo, hydroxy, acetoxy, benzoyloxy, $(C_1-C_4)$ alkylamino, $(C_6-C_{10})$ phenylhydrazino; or $R^1$ and $R^2$ are taken together with the attached carbon to form a carbonyl, $(C_1-C_2)$ ketal, $(C_1-C_2)$ thioketal, hydroxyimino, $(C_1-C_4)$ alkylimino or $(C_6-C_{10})$ phenylhydrazono;

A and B are divalent $(C_1-C_4)$ alkylene groups;

X is methyl or halogen;

$a$ is an integer from 0 to 3;

$n$ is an integer from 0 to 1;

$n'$ is an integer from 0 to 1;

M is a metal selected from the group consisting of calcium, magnesium, manganese, copper, nickel, zinc, iron, cobalt, tin, cadmium, mercury, chromium, lead and barium;

Y is an anion counterion selected from the group consisting of chloride, bromide, iodide, sulfate, bisulfate, phosphate, nitrate, perchlorate, carbonate, bicarbonate, hydrosulfide, hydroxide, acetate, oxalate, malate, citrate and ethylene-bis-dithiocarbamate; and $m$ is an integer from 1 to 4.

2. A metal salt complex according to claim 1 wherein Z is phenyl substituted with up to two substituents selected from the group consisting of fluoro, chloro, bromo, iodo, nitro, trihalomethyl, methyl, ethyl, methoxy and ethoxy;

$R^1$ is hydrogen;

$R^2$ is hydrogen, $(C_1-C_8)$ alkoxy, $(C_2-C_8)$ alkenoxy, or $(C_2-C_8)$ alkynoxy; or $R^1$ and $R^2$ are taken together to form a carbonyl or an ethylene ketal;

A and B are divalent $(C_1-C_4)$ alkylene groups;

X is methyl or halogen;

$a$ is an integer from 0 to 3;

$n$ is 0; and $n'$ is 1.

3. A metal salt complex of claim 2 wherein $R^1$ is hydrogen and $R^2$ is $(C_1-C_8)$ alkoxy, $(C_2-C_8)$ alkenoxy or $(C_2-C_8)$ alkynoxy.

4. A metal salt complex of claim 2 wherein $R^1$ and $R^2$ taken together with the attached carbon atom form an ethylene ketal.

5. A metal salt complex of claim 2 wherein MY is a metal salt of ethylenebisdithiocarbamate.

6. A method for controlling phytopathogenic fungi which comprises applying a fungicidally effective amount of a metal salt complex according to claim 1 to a plant, to plant seeds or to the plant habitat.

7. A method according to claim 6 wherein the metal salt complex is applied to the plant, or the plant habitat at a rate of 0.1 to 50 lbs. per acre.

8. A method according to claim 6 wherein the metal salt complex is applied to the plant seeds at a rate of 0.1 to 20 ounces per hundred pounds of seed.

9. A fungicidal composition which comprises an agronomically acceptable carrier and, as the active ingredient, a fungicidally effective amount of a complex of claim 1.

10. A fungicidal composition which comprises an imidazole free base of the formula

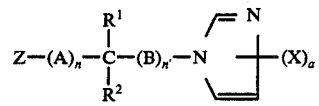

wherein Z is phenyl substituted with up to two substituents selected from the group consisting of fluoro, chloro, bromo, iodo, nitro, trihalomethyl, methyl, ethyl, methoxy and ethoxy; naphthyl; furanyl; benzofuranyl; thienyl or halothienyl;

$R^1$ is hydrogen;

$R^2$ is independently selected from the group consisting of hydrogen, $(C_1-C_8)$ alkoxy, $(C_2-C_8)$ alkenoxy, $(C_2-C_8)$ alkynoxy $(C_1-C_8)$ alkylthio, halo, hydroxy, acetoxy, benzoyloxy, $(C_1-C_4)$ alkylamino $(C_6-C_{10})$ phenylhydrazino; or $R^1$ and $R^2$ are taken together with the attached carbon to form a carbonyl, $(C_1-C_2)$ ketal, $(C_1-C_2)$ thioketal, hydroxyimino, $(C_1-C_4)$ alkylimino or $(C_6-C_{10})$ phenylhydrazono;

A and B are divalent $(C_1-C_4)$ alkylene groups;

X is methyl or halogen;

$a$ is an integer from 0 to 3;

$n$ is an integer from 0 to 1; and $n'$ is an integer from 0 to 1;

and a safening amount of a metal salt selected from the group consisting of zinc chloride, manganese sulfate, cupric bromide, cobaltous nitrate, chromic chloride, ferric sulfate, cadmium nitrate, mercuric chloride, calcium oxalate, calcium carbonate, nickel acetate, stannous iodide, barium hydroxide, magnesium citrate, magnesium perchlorate, lead nitrate, mancozeb, Bordeaux mixture and phenylmercuric acetate in an agronomically acceptable carrier.

* * * * *